(12) United States Patent
Michels (10) Patent No.: US 10,500,351 B2
(45) Date of Patent: Dec. 10, 2019

(54) AID FOR SUBCUTANEOUS TISSUE INJECTION AND PROCESS OF EFFECTING THE INJECTION WITH THE AID

(71) Applicant: Shawn Michael Michels, Oconomowoc, WI (US)

(72) Inventor: Shawn Michael Michels, Oconomowoc, WI (US)

(*) Notice: Subject to any disclaimer, the term of this patent is extended or adjusted under 35 U.S.C. 154(b) by 348 days.

(21) Appl. No.: 15/261,955

(22) Filed: Sep. 11, 2016

(65) Prior Publication Data
US 2017/0232209 A1 Aug. 17, 2017

Related U.S. Application Data

(60) Provisional application No. 62/294,924, filed on Feb. 12, 2016, provisional application No. 62/294,938, filed on Feb. 12, 2016.

(51) Int. Cl.
*A61M 5/42* (2006.01)
*A61M 5/46* (2006.01)

(52) U.S. Cl.
CPC .............. *A61M 5/46* (2013.01); *A61M 5/425* (2013.01)

(58) Field of Classification Search
CPC ................................ A61M 5/46; A61M 5/425
USPC .................................................. 604/115–117
See application file for complete search history.

(56) References Cited

U.S. PATENT DOCUMENTS

| 4,753,636 A | 6/1988 | Free |
| 5,295,972 A | 3/1994 | Mischenko |
| 5,578,014 A | 11/1996 | Erez et al. |
| 6,210,420 B1 | 4/2001 | Mauze et al. |
| 6,537,242 B1 | 3/2003 | Palmer |
| 6,706,049 B2 | 3/2004 | Moerman |

(Continued)

FOREIGN PATENT DOCUMENTS

| EP | 132940 A1 | 6/1984 |
| EP | 1787584 B1 | 7/2012 |

(Continued)

OTHER PUBLICATIONS

Laurent et al.,"Echographic measurement of skin thickness in adults by high frequency ultrasound to assess the appropriate microneedle length for intradermal delivery of vaccines", Vaccine, Jun. 11, 2007, pp. 6423-6430, vol. 25, Elsevier.

(Continued)

*Primary Examiner* — Matthew F Desanto
(74) *Attorney, Agent, or Firm* — Lawrence S. Pope (57) ABSTRACT

The present disclosure is concerned with a device for facilitating a subcutaneous injection and a process for administering the subcutaneous injection. The device has a peripheral frame and an injection needle or an aperture in a central portion of the frame adapted to hold an injection needle. The peripheral frame has an arm or arms adapted to contact the skin at points distant enough from each other to allow the arms or arm to penetrate into the skin a distance greater than the thickness of the skin, a central portion which joins the arms above the terminal portions or portion and an injection needle affixed to the central portion, facing in the same direction as the penetration ends of the arms or an aperture in the central portion adapted to hold an injection needle facing in the same direction as the penetration ends of the arms.

20 Claims, 6 Drawing Sheets

(56) References Cited

U.S. PATENT DOCUMENTS

| | | | |
|---|---|---|---|
| 6,913,593 | B1 | 7/2005 | Alexandre et al. |
| 7,744,582 | B2 | 6/2010 | Sadowski et al. |
| 8,632,503 | B2 | 1/2014 | Ruan et al. |
| 9,216,256 | B2 | 12/2015 | Olson et al. |
| 9,717,861 | B2 * | 8/2017 | Banik ................. A61M 5/3287 |
| 2002/0058907 | A1 | 5/2002 | Deboer et al. |
| 2007/0021716 | A1 | 1/2007 | Hansen |
| 2008/0114298 | A1 * | 5/2008 | Cantor .............. A61M 37/0015 604/117 |
| 2013/0096502 | A1 | 4/2013 | Kawamoto et al. |
| 2015/0258284 | A1 | 9/2015 | Fenster et al. |
| 2018/0021526 | A1 | 1/2018 | Sullivan et al. |
| 2018/0326163 | A1 | 11/2018 | Bailey |

FOREIGN PATENT DOCUMENTS

| | | | |
|---|---|---|---|
| EP | 2589401 | A1 | 5/2013 |
| GB | 2544499 | A | 11/2015 |
| GB | 2544580 | A | 8/2016 |
| JP | 4118399 | B2 | 5/2008 |
| JP | 2008110260 | A1 | 5/2008 |
| WO | 9934850 | A1 | 7/1999 |
| WO | 0187389 | A1 | 11/2001 |
| WO | 2001/93931 | A1 | 12/2001 |
| WO | 2004/045375 | A2 | 6/2004 |
| WO | 2010/030965 | A2 | 3/2010 |
| WO | 2011/039736 | A2 | 4/2011 |

OTHER PUBLICATIONS

Lim et al., "Ultrasound-guided measurement of skin and subcutaneous tissue thickness in children with diabetes and recommendations for giving insulin injection", Journal of Clinical & Translational Endocrinology, Jun. 2018, pp. 26-35, vol. 12, Elsevier.

Office Action of 20 Aug. 2019 in Japanese Patent Application 2018-561183 X.

* cited by examiner

AID FOR SUBCUTANEOUS TISSUE INJECTION AND PROCESS OF EFFECTING THE INJECTION WITH THE AID

RELATED APPLICATIONS

This application claims priority to U.S. Provisional Application Ser. Nos. 62/294,924 and 62/294,938, both filed 12 Feb. 2016 and both incorporated herein by reference.

BACKGROUND

Subcutaneous injection is a means of administering therapeutics that requires proper placement of the injection needle. The therapeutic needs to be injected beneath the skin but not into the underlying muscle tissue. The injection site is a substantial factor in controlling the rate of systemic disbursement of the therapeutic and the dosage regimens of a significant number of therapeutics are keyed to their administration to subcutaneous tissue.

The proper placement of the injection needle is typically achieved by controlling the depth of its penetration beneath the skin and this in turn can be controlled by how far the needle is advanced into and through the skin and the angle between the needle and the skin. One approach has been to pinch the skin and underlying subcutaneous tissue and insert the injection needle into the gathered tissue. However, this approach requires the use of two hands. It also limits the injection sites to those where there is adequate tissue to be pinched.

Commonly the injection needle is fitted to a syringe and the syringe is used to direct the placement of the injection needle. The proper placement of the injection needle with this mechanical arrangement can require considerable manual dexterity and may be particularly difficult in circumstances in which there is movement of the patient or the syringe, for instance when administration is attempted on a moving conveyance like a car or train.

Typically the faster the injection needle is inserted into the tissue the less pain that is experienced. However, the insertion may be slower than optimum because of the mechanical arrangement. The insertion may proceed slowly out of a concern to achieve proper positioning of the injection needle.

Some discomfort may be experienced if the injection needle moves after insertion and before the therapeutic is fully dispersed. The mechanical arrangement of the syringe located at a considerable distance from the end of the insertion needle being the sole means of controlling the ends location, enhances the probability of such movement and resultant discomfort. This in turn may cause a premature withdrawal of the injection needle before the therapeutic is fully administered.

SUMMARY

The present invention involves a device for facilitating a subcutaneous injection into a patient and a process for administering a subcutaneous injection. The device may have a peripheral frame and an injection needle or an aperture in a central portion of the frame adapted to hold an injection needle. The peripheral frame has two or more arms or a continuous arm adapted to contact the skin of the patient at points distant enough from each other to allow the arms or arm to penetrate into the skin a distance greater than the thickness of the skin, a central portion which joins the arms at a vertical height above the terminal portions or portion of the arms or arm adapted to contact the skin greater than the intended penetration distance of the arms and an injection needle affixed to the central portion, facing in the same direction as the penetration ends of the arms and of sufficient length to penetrate through the skin and into the subcutaneous tissue when these ends penetrate into the skin or an aperture in the central portion adapted to hold an injection needle facing in the same direction as the penetration ends of the arms, the needle being of sufficient length and held an appropriate vertical distance from these ends to penetrate through the skin and into the subcutaneous tissue when these ends penetrate into the skin.

The device may have one or more skin penetration plates that both have a sufficiently small skin contacting area and encompass a sufficient area of skin within their perimeter to allow the plates to penetrate into the skin a distance greater than the thickness of the skin, a central portion centered above the encompassed area of skin, an injection needle affixed to the central portion, facing toward the skin penetration plate or plates and of sufficient length to penetrate through the skin and into the subcutaneous tissue when this plate or these plates penetrate into the skin or an aperture in the central portion adapted to hold an injection needle facing in the same direction as the penetration plate or plates, the needle being of sufficient length and held an appropriate vertical distance from this plate or these plates to penetrate through the skin and into the subcutaneous tissue when this plate or these plates penetrate into the skin; and support arms connecting the skin penetration plate or plates to the central portion.

The process involves obtaining the device, in the case in which the central portion does not already have the injection needle in place, affixing the injection needle in the aperture and pressing the peripheral frame against the skin of a patient such that the injection needle penetrates through the skin into the subcutaneous tissue without penetrating into any muscle tissue.

DETAILED DESCRIPTION

Figure 1:
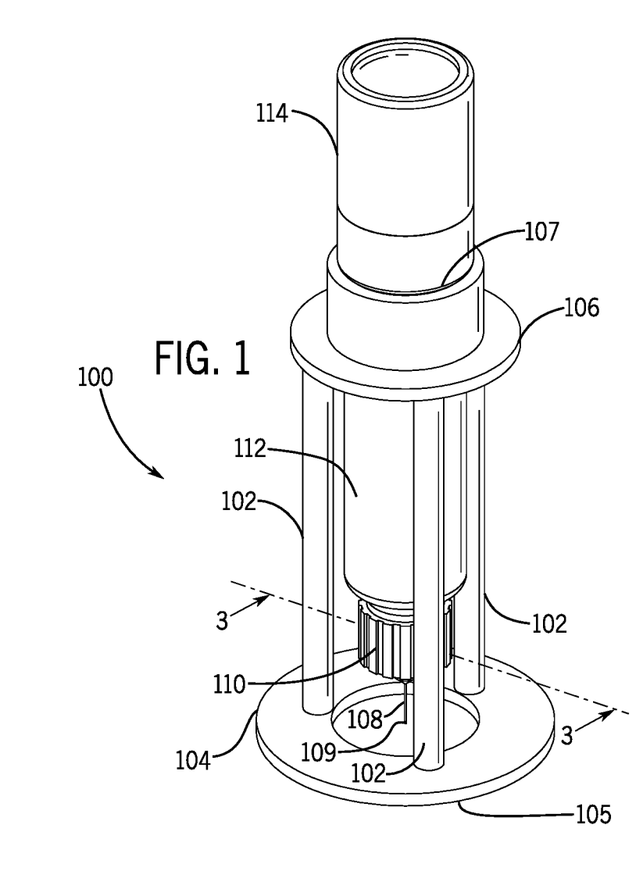
FIG. 1 is a perspective view of a peripheral frame or device with a syringe mounted in it.

Referring to FIG. 1, a peripheral frame or device 100 is illustrated in combination with a syringe. The frame or device has arms 102 that terminate at one end in a common circular penetration end or plate 104. It is also possible for each arm 102 to have its own penetration end or plate and it is also possible for there to be a single arm 102. The arms 102 terminate at the other end in a central portion 106. This central portion 106 has an aperture 107 into which the body 112 of a syringe has fixed such that the special relationship between the frame or device and the syringe is fixed. One skilled in the art will recognize that there are many ways or fixing the body 112 such as a rubber insert that frictionally engages both the aperture 107 and the body 112. Such an insert might be knurled. Affixed to the terminal end of the body 112 is a syringe cap 110 that carries an injection needle 108 with a terminal end 109. At the opposite end of the syringe body is a plunger 114 which may be activated to dispense a therapeutic retained in the interior of the body 112 through the injection needle 108. The peripheral frame or device 100 is adapted to facilitate the proper placement of the injection needle 108 and especially its terminal end 109. It is convenient to facilitate locating this end 109 in the subcutaneous tissue of a patient to whom the therapeutic is being administered or self-administered.

Figure 2:
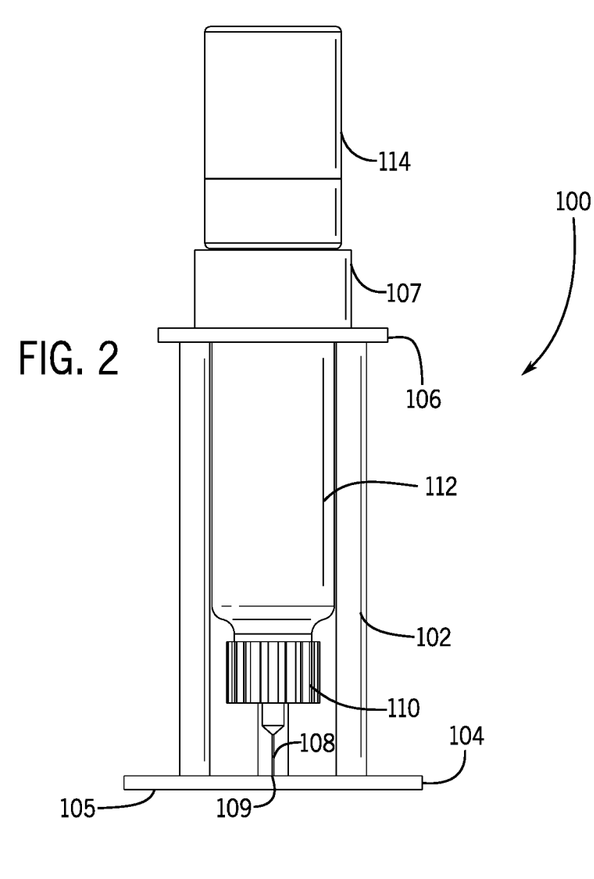
FIG. 2 is a side elevation of the same peripheral frame or device with a syringe mounted in it.

Referring to FIG. 2, the syringe body 112 has been fixed to the central portion 106 of the frame or device 100 via the aperture 107 such that there is a fixed special relationship between the frame or device and the injection needle 108 and its terminal end 109. Taking into account the relationship between the arms 102, the penetration end or plate 104 and the central portion 106 that carries the aperture 107, this means there is a fixed special relationship between the terminal end 109 of the injection needle 108 and the bottom 105 of the penetration end or plate 104. It is convenient if the vertical distance between them is such that when the penetration ends have compressed the flesh of a patient utilizing the frame or device 100 the injection needle 108 penetrates into but not through the subcutaneous tissue of the patient. This is typically between about 1 mm and 3 mm. Because the penetration ends or plates typically need to be fairly rigid to achieve the desired penetration into the flesh, it may be advantageous to cover them with a cushioning material for the comfort of the patient. But in such cases an appropriate adjustment should be made to account for the compressed thickness of the cushioning material in establishing this vertical distance difference. In this regard, different cushioning materials could be used to adjust for patients with different skin and subcutaneous tissue characteristics such as the difference between adults and children.

Figure 3:
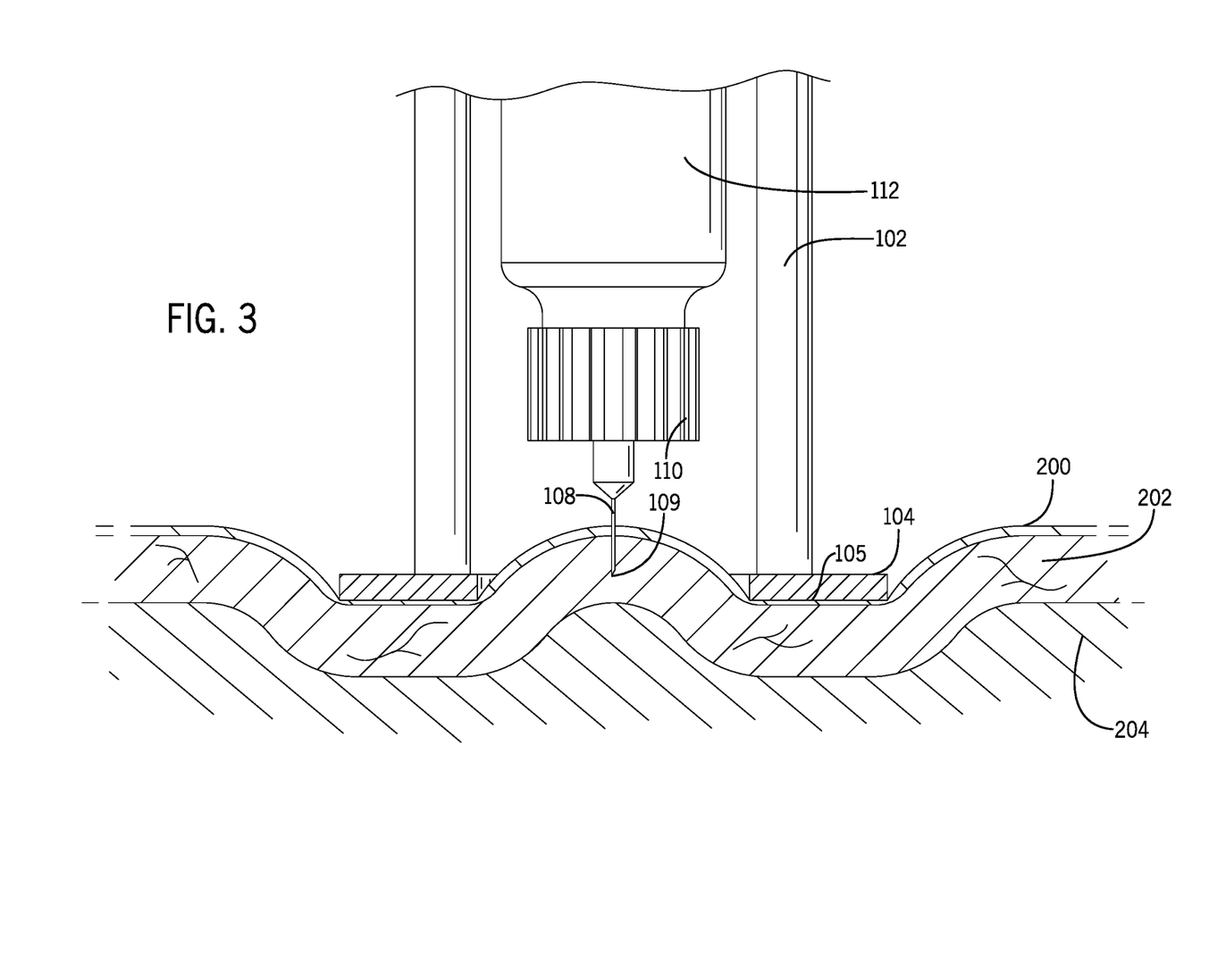
FIG. 3 is a cross-section along line 3 of FIG. 1 of the peripheral frame or device interacting with the tissue of a patient.

Referring to FIG. 3, the frame or device 100 has been pressed against the flesh of a patient utilizing the frame or device 100 such that the skin 200 has been compressed and the injection needle 108 has penetrated into the subcutaneous tissue 202 of the patient, but the terminal end 109 of this needle 108 has not penetrated into muscle tissue 204, the syringe body 112 and the syringe cap 110 have acted to maintain a fixed special relationship between the injection needle 108 and the penetration end or plate 104. The cap 110 is fixed on the terminal end of the body 112 and the mid-section of the body 112 is fixed to the central portion 106 (not shown in this FIG.) and the penetration end or plate 104 is also fixed to the central portion 106 via the arms 102.

Figure 4:
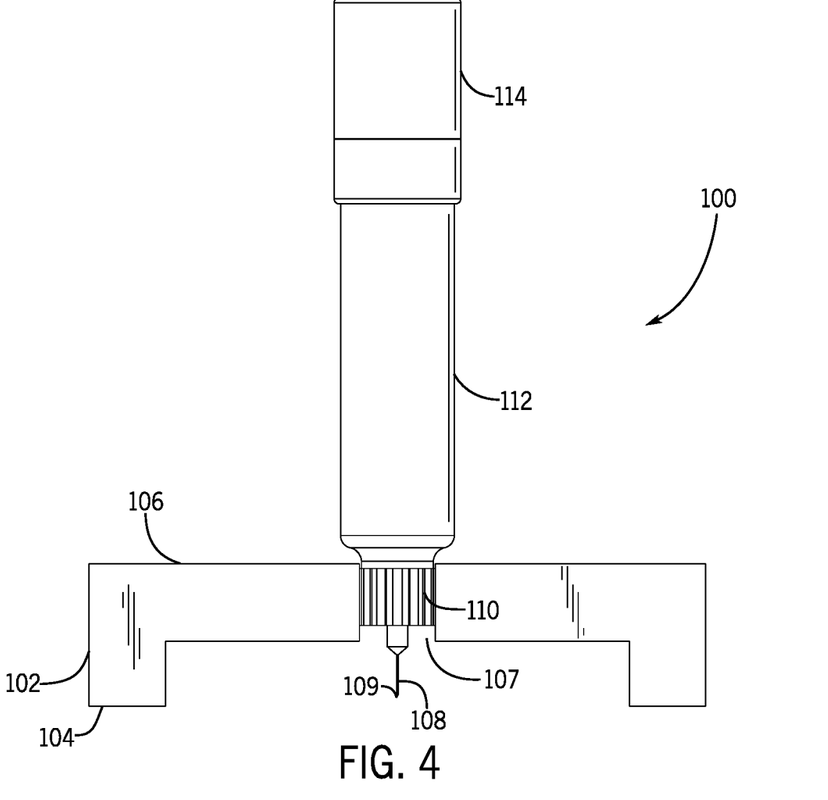
FIG. 4 is a side elevation of an alternative embodiment of the peripheral frame or device.

Referring to FIG. 4, a different embodiment of the peripheral frame or device 100 is illustrated in combination with a syringe. In this embodiment each of the legs 102 terminates in its own penetration end or plate 104. Unlike the embodiment illustrated in FIG. 1-3, the penetration ends 104 do not form a closed polygon, but rather are just two rectangles equally spaced from the injection needle 108. However, they are spaced such that when the device 100 is pressed into the flesh of a patient the syringe body 112 and the syringe cap 110, which is held in the aperture 107 of the central portion 106, interact with these penetration ends 104 such that the injection needle 108 penetrates into the subcutaneous tissue of the patient without its terminal end 109 extending into the patients muscle tissue.

Figure 5:
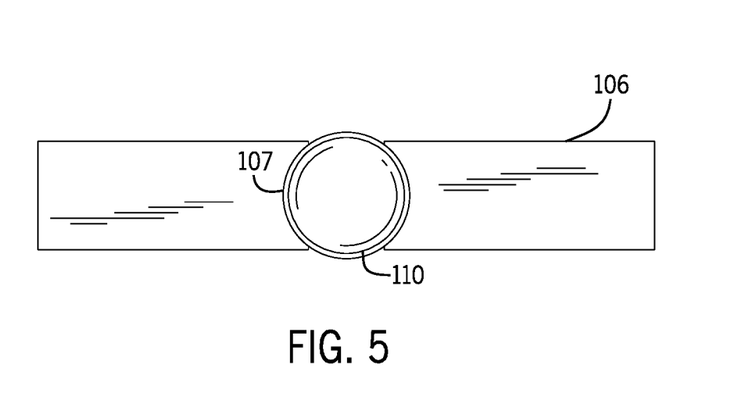
FIG. 5 is a top view of the peripheral frame or device of FIG. 4.

Referring to FIG. 5, it can be seen that the central portion 106 of this embodiment with its aperture 107 and attached syringe cap 110 does not entirely surround any portion of the patient's flesh.

Figure 6:
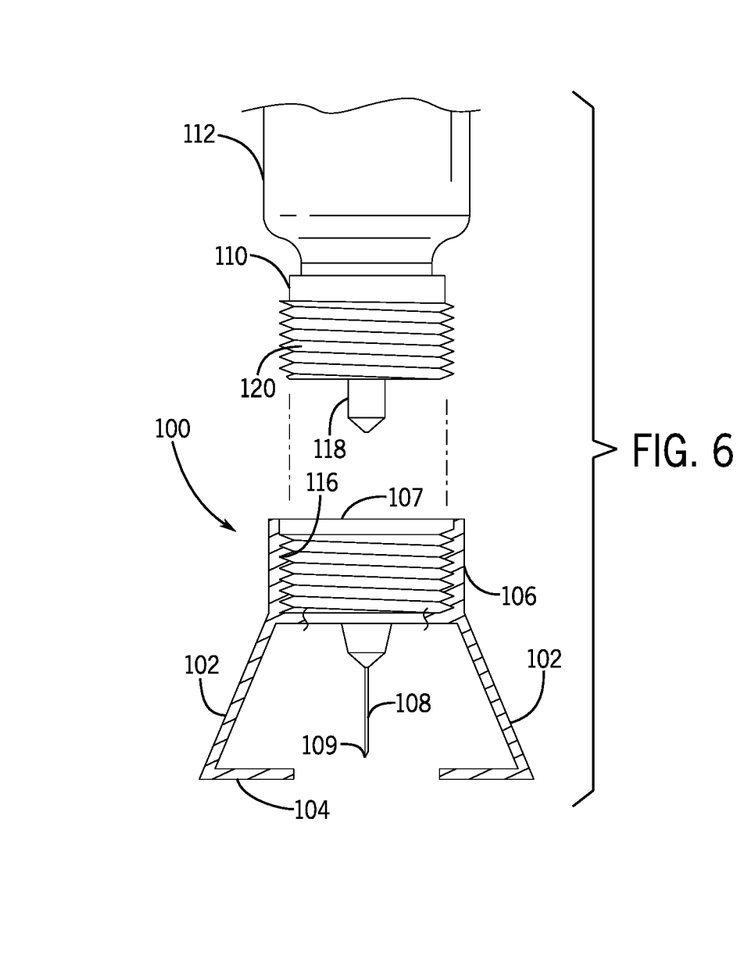
FIG. 6 is a side cross section of an alternative embodiment of the peripheral frame or device with an injection needle as an integral part.

Referring to FIG. 6, a different embodiment of the peripheral frame or device 100 is illustrated in combination with a modified syringe. This modified syringe has a cap 110 that carries threads 120 and a nose 118. This allows it to interact with a central portion 106 that has an aperture 107 that carries threads 120. This central portion 106 also carries the injection needle 108. The relationship between the penetration end or plate 104 of the legs 102 is such that the terminal end 109 of the injection needle 108 will penetrate into the subcutaneous tissue of a patient without extending into the muscle tissue of the patient when the device 100 is pressed against the flesh of the patient.

Figure 7:
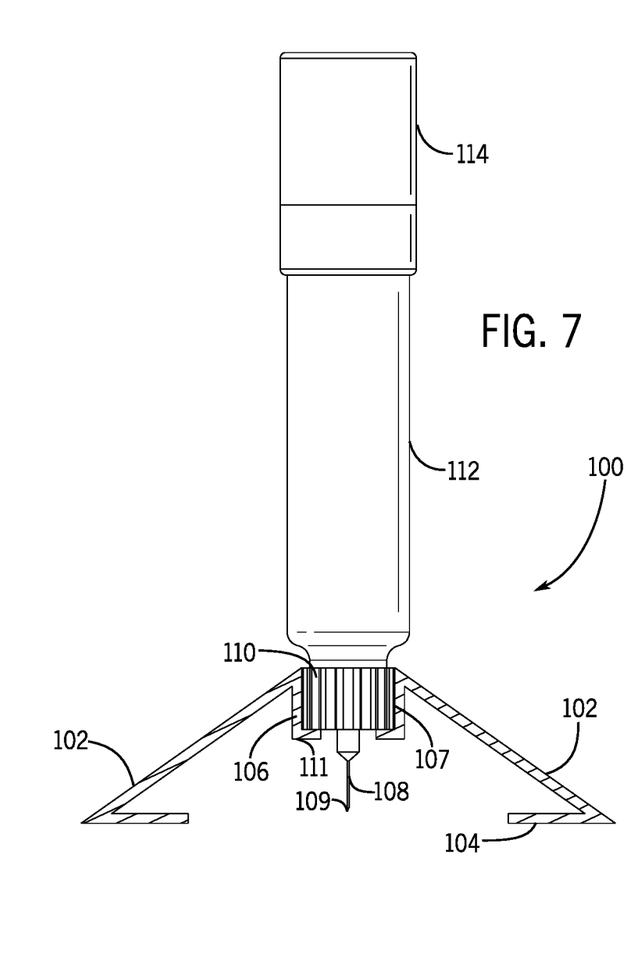
FIG. 7 is a side cross section of an alternative embodiment of the peripheral frame or device with a downward projection.

Referring to FIG. 7, a different embodiment of the peripheral frame or device 100 is illustrated in combination with a syringe. In this case the syringe body 112 is connected to the central portion 106 via its cap 110 using an aperture 107 that has a bottom wall 111 that assures the vertical positioning of the injection needle 108 relative to the penetration end or plate 104 or arm 102. Thus when the device 100 is pressed against the flesh of the patient the terminal end 109 of the injection needle 108 will penetrate into the subcutaneous tissue of a patient without extending into the muscle tissue of the patient.

Figure 8:
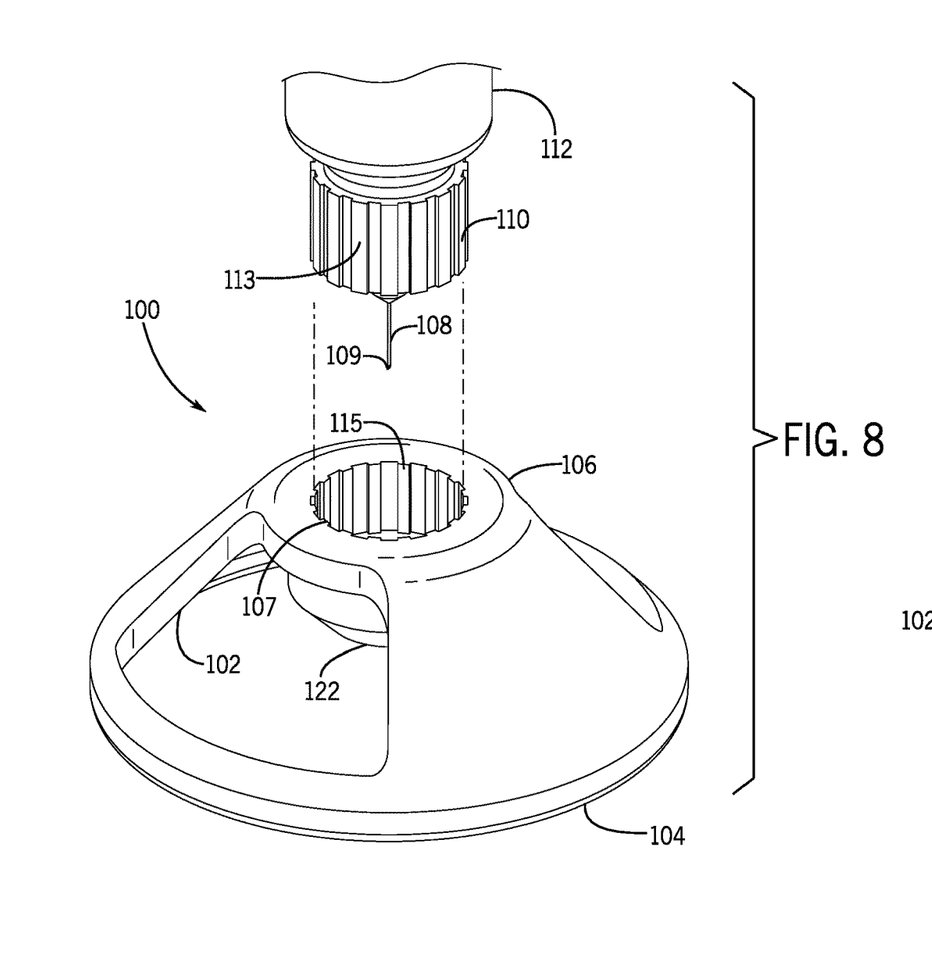
FIG. 8 is a perspective view an alternative embodiment of the peripheral frame or device with a circular penetration end or plate.

Referring to FIG. 8, a different embodiment of the peripheral frame or device 100 is illustrated in combination with a syringe. The syringe cap 110 is provided with a series of vertical protrusions 113 that mate with a series of vertical slots in the aperture 107 of the central portion. The aperture 107 of the central portion 106 is also provided with a downward protrusion 122. There is essentially a single continuous arm 102 that terminates in a single penetration end or plate 104 that is in the form of a circle. The aperture 107 may alternatively have a rubber insert which securely holds the syringe cap 110 or the aperture 107 may have a smooth wall dimensioned to securely hold the syringe cap 110.

Figure 9:
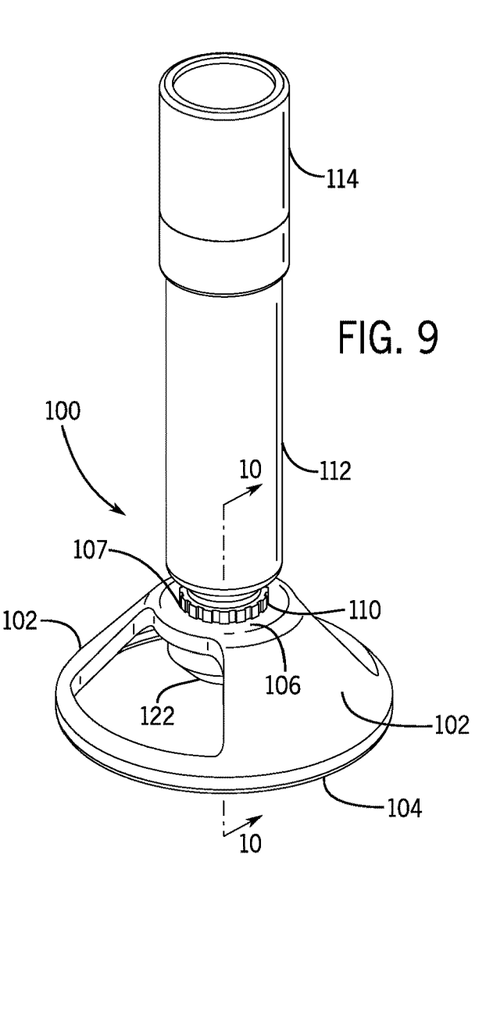
FIG. 9 is a perspective view of the peripheral frame or device of FIG. 8 interaction with a syringe.

Referring to FIG. 9, the relationship of the syringe plunger 114, the syringe body 112 and the syringe cap 110 to the frame or device is illustrated for the embodiment of FIG. 8.

Figure 10:
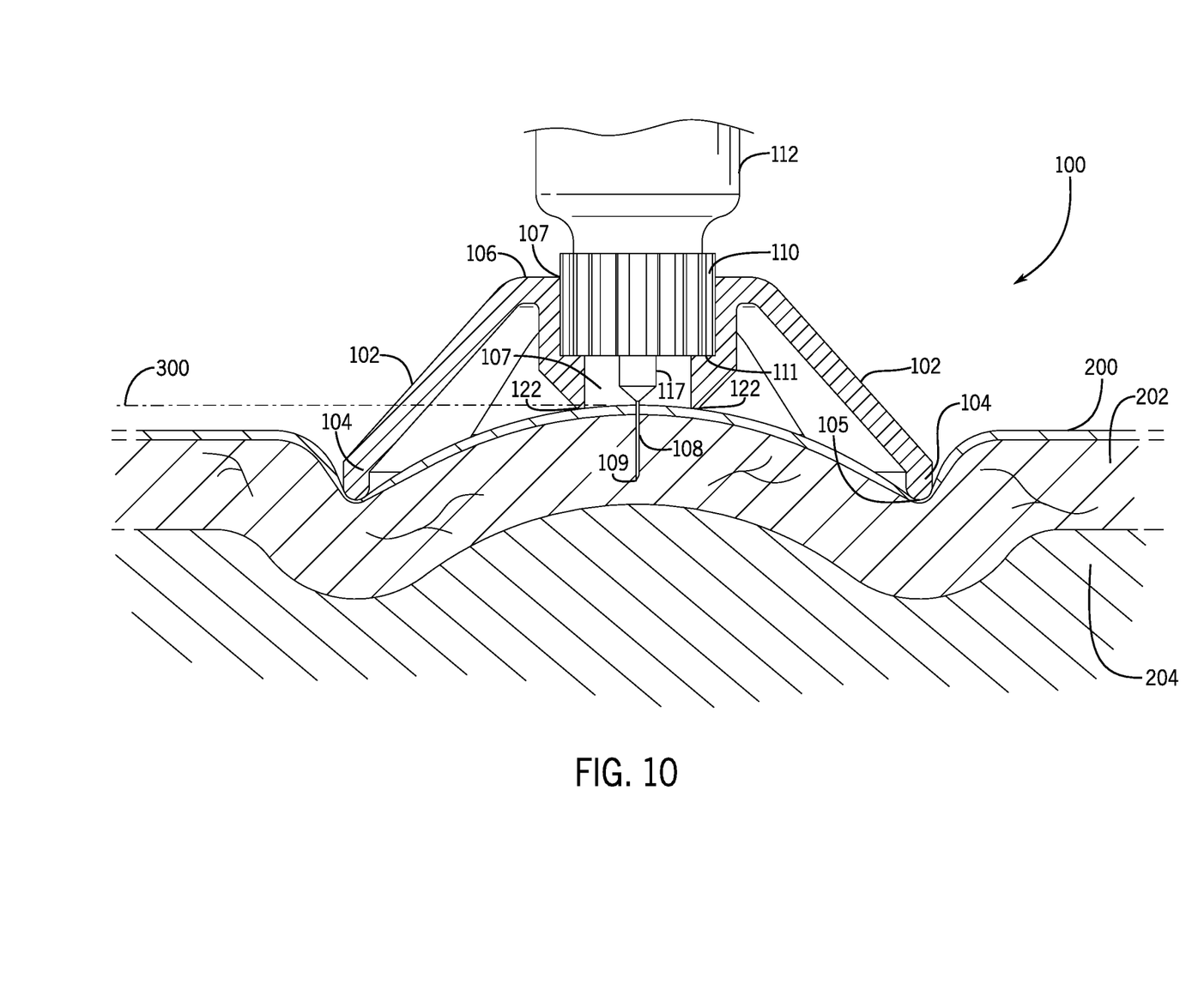
FIG. 10 is a side cross section of the peripheral frame or device of FIG. 8 with a syringe in place interacting with the tissue of a patient.

Referring to FIG. 10, a cross section along line 10 of FIG. 9 illustrates the interaction of this embodiment with the flesh of a patient. The aperture 107 of the central portion 106 not only has a bottom wall 111 but also has a downward protrusion 122. This protrusion 122 surrounds the connector 117 of the syringe cap 110 Thus it can act to control the depth of penetration of the injection needle 108. The penetration end or plate 104 compresses the skin 200 and projects into the subcutaneous tissue 202. This mechanically allows the central portion 106 to move toward the skin 200 and the injection needle 108 to penetrate through the skin 200 and into the subcutaneous tissue 202. However, the frame or device 100 is designed such that the terminal end 109 of the injection needle 108 does not enter the muscle tissue 204. As a result of the downward pressure of the penetration end or plate 104, the skin does rise a bit in the area encompassed by the penetration end or plate 104 as indicated by the line 300. Typically this rise is about 1 mm. It has been found convenient for the inside diameter of the penetration end or plate 104 to be about 4.1 cm and its width in the plane of the skin to be 0.2 cm. It is also convenient to use a 4, 5, 6, or 8 mm long injection needle 108 whose terminal end 109 is positioned about 1-3 mm higher than the bottom surface 105 of the penetration end 104.

Typical dimensions of the frame or device may relate to the dimensions of readily available injection needles and the need to encompass sufficient tissue to allow adequate penetration of the penetration ends or plates. It is convenient to allow between about 3 mm and 11 mm, preferably between about 5 mm and 9 mm between the penetration end of one of the arms and the upper end of the penetration needle. It is also convenient to provide a vertical distance between the penetration end of one of the arms and the lower end of the penetration needle between about 1 mm and 3 mm. It is also convenient to use penetration ends or plates that readily allow penetration and those with a width of surface that contact the skin is between about 0.1 and 0.3 cm are helpful. It is further helpful to have a horizontal distance between penetration ends or plates of between about 2 cm and 6 cm. Adequate penetration is also facilitated if the area encompassed by the penetration ends or plates is between about 10 cm$^2$ and 20 cm$^2$.

The figure formed by the penetration end or ends in the plane of the skin of a patient before pressure is applied is virtually unlimited. For manufacturing ease it may be any regular polygon such as an equilateral triangle, a square, a pentagon or a hexagon. It also may be a smooth curve such as an ellipse or a circle. Irregular shapes will function as well but the manufacturing of irregular shapes is more challenging, but provides no particular advantage.

For ease of description reference has been made to a syringe or a modified syringe, but any device that can deliver a therapeutic to an injection needle at a gradual rate is suitable. In this regard, syringe has been used in a broad sense to include any device with a cylinder for holding a therapeutic that can be delivered through an injection needle associated with a plunger or activator that operates to drive the therapeutic through the injection needle. Typically the injection needle has a fluid tight direct connection with the holding cylinder of the syringe, although other fluid paths are possible, such as the modified syringe described in association with FIG. 6. Thus syringe has been used in a sense that encompasses an injection pen. Other delivery devices that can benefit from the frame or device of the present invention in administering subcutaneous injections include the auto injectors that can deploy or "fire" an injection needle upon activation such as that described in US Published Patent Application 2015/0258284. Typically the operation of such devices would be modified so as to rely the forward progress of the frame or device of the present invention for insertion of the injection needle into subcutaneous tissue. For instance, the auto injector could be first activated and then carried forward with the frame or device of the present invention when it is pressed against the flesh of a patient.

The peripheral frame or device of the present invention can be applied to a wide variety of sites on the human body, virtually anywhere where there is an adequate area to accommodate it. However, it may be advantageous to apply it to tissue that shows crease lines when it is flexed, such as the abdomen, and, if the frame is constructed with parallel separate penetration end or plates, to align them parallel to these crease lines.

The peripheral frame or device of the present invention can be beneficially used to aid the delivery of any fluid therapeutic that is to delivered by subcutaneous injection including insulin. It can be adapted to interact with any delivery device that relies upon an injection needle to assure placement of the delivery end of the injection needle in subcutaneous tissue.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A device for facilitating a subcutaneous injection into a patient comprising:
   a. a peripheral frame having
      i. two or more arms having penetration ends or a continuous arm having a penetration end adapted to contact skin of the patient at points distant enough from each other to allow the arms or arm to penetrate without piercing into the skin a distance, measured from the unperturbed surface of the skin, greater than the thickness of the skin; and
      ii. a central portion which joins the arms or continuous arm at a vertical height above said penetration ends or end greater than the intended penetration distance of the arms or arm, wherein the central portion has a downward projection that is short enough to avoid preventing the arm or arms from penetrating the skin a thickness greater than the thickness of the skin; and
   b. an injection needle having an upper end and a lower end affixed to the central portion, facing in the same direction as said the penetration ends or end and of sufficient length to penetrate with piercing through the skin and into the subcutaneous tissue when these ends penetrate without piercing into the skin,
   wherein the vertical distance between one of said penetration ends and the exposed upper end of the injection needle is between about 3 mm and 11 mm, and the vertical distance between the said penetration end and the lower end of the injection needle is at least about 1 mm in order for the injection needle to penetrate with piercing through the skin into the subcutaneous tissue without penetrating into any muscle tissue.

2. The device of claim 1 wherein the penetration ends of the arms form a closed polygon or curve.

3. The device of claim 2 wherein there are two penetration arms with about equal sized penetration ends whose midpoints are spaced 180° from each other and whose edges are spaced from each other.

4. The device of claim 3 wherein the edges of the penetration ends of each arm are spaced from the edges of the other penetration end by at least about the horizontal length of that penetration end.

5. The device of claim 1 wherein the downward projection at least partially surrounds the upper end of the injection needle and limits the movement of the central portion toward the skin.

6. The device of claim 5 wherein the projection terminates at about the same vertical height as the exposed upper end of the injection needle.

7. The device of claim 6 wherein the projection is spaced from the upper end of the injection needle in the horizontal plane in which they both lie.

8. The device of claim 1 wherein the patient is a human.

9. The device of claim 1 wherein the vertical distance between the penetration end of one of the arms and the lower end of the injection needle is between about 1 mm and 3 mm.

10. The device of claim 1 wherein the width of surface of the penetration arm or arms that contact the skin is between about 0.1 and 0.3 cm.

11. The device of claim 1 wherein the horizontal distance between the penetration ends of the arms is between about 2 cm and 6 cm.

12. The device of claim 1 wherein the area within the penetration ends or end of the arms or arm is between about 10 $cm^2$ and 20 $cm^2$.

13. The device of claim 1 wherein the relationship between the injection needle and the penetration end or ends of the arm or arms is such that the needle does not penetrate beyond the subcutaneous tissue when the device is applied to a typical adult human.

14. The device of claim 1 wherein the central portion has an aperture.

15. The device of claim 1 wherein the injection needle is designed to penetrate with piercing more than 3 mm.

16. A device for facilitating a subcutaneous injection into a patient comprising:
   a. one or more skin penetration plates that both have a sufficiently small skin contacting area and encompass a sufficient area of skin within their perimeter to allow the plates to penetrate without piercing into the skin a distance, measured from the unperturbed surface of the skin, greater than the thickness of the skin;
   b. a central portion centered above the encompassed area of skin, wherein the central portion has a downward projection that is short enough to avoid preventing the arm or arms from penetrating the skin a thickness greater than the thickness of the skin;
   c. an injection needle affixed to the central portion, facing toward the skin penetration plate or plates and of sufficient length to penetrate through the skin and into the subcutaneous tissue when this plate or these plates penetrate without piercing into the skin; and
   d. support arms connecting the skin penetration plate or plates to the central portion,
   wherein the vertical distance between said skin penetration plate and the exposed upper end of the injection needle is between about 3 mm and 11 mm, and the vertical distance between the said skin penetration plate and the lower end of the injection needle is at least about 1 mm in order for the injection needle to penetrate with piercing through the skin into the subcutaneous tissue without penetrating into any muscle tissue.

17. The device of claim 16 wherein:
   a. the one or more skin penetration plates is a single skin penetration plate which has a central aperture of sufficient size to allow the plate to penetrate without piercing into the skin a distance greater than the thickness of the skin;
   b. the downward projection at least partially surrounds the upper end of the injection needle and limits the movement of the central portion toward the skin;
   c. the device is designed to be used with a human patient; and
   d. the relationship between the injection needle and the penetration plate or plates is such that the needle does not penetrate beyond the subcutaneous tissue when the device is applied to a typical adult human.

18. The device of claim 17 wherein the support arms join the central portion at an acute angle.

19. The device of claim 16 wherein the injection needle is designed to penetrate with piercing more than 3 mm.

20. A process for administering a subcutaneous injection to a human patient comprising:
   a. obtaining a peripheral frame having
      i. two or more arms having penetration ends or a continuous arm having a penetration end adapted to contact skin of the patient at points distant enough from each other to allow the arms or arm to penetrate without piercing into the skin a distance, measured from the unperturbed surface of the skin, greater than the thickness of the skin;
      ii. a central portion which joins the arms or continuous arm at a vertical height above said penetration ends or end greater than the intended penetration distance of the arms or arm, wherein the central portion has a downward projection that is short enough to avoid preventing the arm or arms from penetrating the skin a thickness greater than the thickness of the skin; and
      iii. an aperture in the central portion adapted to hold an injection needle facing in the same direction as said penetration ends or end,;
   b. affixing an injection needle in the aperture, the needle being of sufficient length and held an appropriate vertical distance from these ends to penetrate with piercing through the skin and into the subcutaneous tissue when these ends penetrate or this end penetrates without piercing into the skin; and
   c. pressing the peripheral frame against the skin of a patient such that the injection needle penetrates with piercing through the skin into the subcutaneous tissue without penetrating into any muscle tissue,
   wherein the vertical distance between one of said penetration ends and the exposed upper end of the injection needle is between about 3 mm and 11 mm, and the vertical distance between the said penetration end and the lower end of the injection needle is at least about 1 mm in order for the injection needle to penetrate with piercing through the skin into the subcutaneous tissue without penetrating into any muscle tissue.

* * * * *